United States Patent [19]

Failli

[11] Patent Number: 4,859,671
[45] Date of Patent: Aug. 22, 1989

[54] 2-SUBSTITUTED 1,2-BENZISOTHIAZOL-3(2H)-ONE 1,1-DIOXIDE USEFUL AS AN ANXIOLYTIC AGENT

[75] Inventor: Amedeo A. Failli, Princeton Junction, N.J.

[73] Assignee: American Home Products Corporation, New York, N.Y.

[21] Appl. No.: 216,922

[22] Filed: Jul. 8, 1988

[51] Int. Cl.$^4$ .................. A61K 31/495; C07D 417/14
[52] U.S. Cl. ...................................... 514/254; 544/362
[58] Field of Search ......................... 544/362; 514/254

[56] References Cited

U.S. PATENT DOCUMENTS

| 3,717,634 | 2/1973 | Wu et al. | 544/230 |
| 4,001,223 | 1/1977 | Sugimoto | 544/386 |
| 4,202,898 | 5/1980 | Depoortere | 544/394 |

OTHER PUBLICATIONS

Fozard et al, British Journal of Pharmacology.

Primary Examiner—Cecilia Shen
Attorney, Agent, or Firm—Walter Patton

[57] ABSTRACT

There is disclosed the compound 2-[4-[4-(2,7-naphthyridin-1-yl)-1-piperazinyl]butyl]-1,2-benzisothiazol-3(2H)-one 1,1-dioxide, and the method of producing said compound, and the pharmaceutically acceptable salts thereof, and the use of said compound as an anxiolytic agent having a low liability for extrapyramidal side effects.

3 Claims, No Drawings

2-SUBSTITUTED 1,2-BENZISOTHIAZOL-3(2H)-ONE 1,1-DIOXIDE USEFUL AS AN ANXIOLYTIC AGENT

BACKGROUND OF THE INVENTION

The recent introduction of buspirone having a selectivity for $5\text{-}HT_{1A}$ receptors, as an effective anxiolytic agent U.S. Pat. No. 3,717,634), into the U.S. marketplace has stimulated interest in development of second-generation anxiolytic agents.

Furthermore, in clinical trials, gepirone and ipsapirone were found to be potent anxiolytic drugs. Since both drugs—gepirone and ipsapirone—possess a higher degree of selectivity for $5\text{-}HT_{1A}$ receptors than buspirone, the clinical data supports the notion that anxiety mechanisms can be directly modulated by $5\text{-}HT_{1A}$ receptor drug interactions.

In addition to treatment of anxiety, $5\text{-}HT_{1A}$ agonists such as gepirone are now being examined for their mixed activity as anxiolytic antidepressant agents. The therapeutic potential of $5\text{-}HT_{1A}$ agonists in the treatment of multi-CNS disorders was recently extended to the development of antipsychotic anxiolytic agents represented by MDL-72832 and KS-9172 (Br. J. Pharmacol., 90, 273P, 1987), the latter being under development as an antipsychotic agent (Scrip No. 1265, Dec. 11, 1987). This class of compounds demonstrated high affinity for both the $5\text{-}HT_{1A}$ and $D_2$ receptor binding sites.

PRIOR ART

U.S. Pat. No. 4,202,898 describes arylpiperazines useful for the treatment of anxiety and depression. U.S. Pat. No. 4,001,223 describes the synthesis of adamantane derivatives useful as cerebral vasodilators.

U.S. Pat. No. 4,202,898 discloses synthesis of arylpiperazines of the general formula

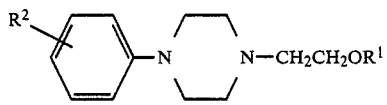

wherein $R^1$ is H, CO (lower alkyl), CO (monocyclic aryl), CONH (lower alkyl), CON (lower alkyl) or CONH (monocyclic aryl); $R^2$ is H, alkyl, alkoxy, CN, halo or trifluoromethyl useful for the treatment of anxiety and depression.

DESCRIPTION OF THE INVENTION

The present invention relates to the novel compound 2-[4-[4-(2,7-naphthyridin-1-yl)-1-piperazinyl]butyl]-1,2-benzisothiazol-3(2H)-one 1,1-dioxide having CNS activity and having the formula

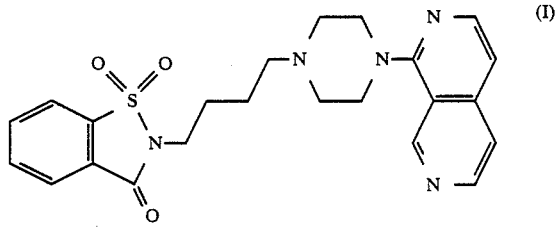

and the pharmaceutically acceptable salts thereof.

The compound of the invention can form pharmacologically acceptable salts from pharmacologically acceptable organic and inorganic acids such as hydrochloric, hydrobromic, sulfonic, sulfuric, phosphoric, nitric, maleic, fumaric, benzoic, ascorbic, pamoic, succinic, methanesulfonic, acetic, propionic, tartaric, citric, lactic, malic, mandelic, cinnamic, palmitic, itaconic and benzenesulfonic.

The compound of this invention may exist either in the form of the free base or the pharmacologically acceptable salts. Methods for converting one such form to another will be obvious to one skilled in the chemical arts.

The compound of this invention demonstrates affinity for the $5\text{-}HT_{1A}$ receptor site and is useful as an anxiolytic agent.

The compound of the invention displays a preclinical pharmacological profile like that of the compound gepirone(4,4-dimethyl-1-[4-[4-(2-pyrimidinyl)-1-piperazinyl]butyl]-2,6-piperidinedione) and ritanserin 6-[2-[4-[bis(4-fluorophenyl)methylene]-1-piperidinyl]-7-methyl-5H-thiazolo[3,2-a]pyrimidin-5-one. Gepirone and ritanserin have demonstrated clinical activity in anxiolytic and antidepressant paradigms and have also displayed a unique clinical anxioselective profile, whereby their efficacy in the treatment of anxiety neuroses is comparable to the benzodiazepine diazepam. Additionally, most chronically used antipsychotic drugs cause exta-pyramidal side effects, such as pseudo-parkinsonism, tardive dyskinesia and the like. Ideally, treatment of depression, psychoses and anxiety should be free of any undesirable side effects. The compounds of the invention, in a manner similar to ritanserin and buspirone, may display preclinical anxiolytic and antidepressant activities with expected minimal side effects.

When employed as an anxiolytic or antidepressant, the effective dosage of the active substance for such treatment will vary according to the severity and nature of the condition being treated. Therapy should be initiated at lower doses (in mg/kg/day), the dosage thereafter being increased, if necessary, to produce the desired effect. In general, the compound of the invention is most desirably administered at a concentration that will generally afford effective results without causing any harmful or deleterious side effects.

When the compound of the invention is employed as an anxiolytic or an antidepressant agent, it can be formulated into oral dosage forms such as tablets, capsules and the like. The compound can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compound may be encapsulated with or without other carriers. In all cases, the proportion of active ingredient in said compositions both solid and liquid will be sufficient at least to impart the desired activity thereto on oral administration. The compound may also be injected parenterally in which case it is used in the form of a sterile solution containing other solutes, for example, enough saline or glucose to make the solution isotonic.

The antidepressant activity of the compound of the invention and its expected lack of extrapyramidal side effects may be demonstrated by standard pharmacological procedures, which are described more fully in the examples given hereafter.

The following examples show the preparation and pharmacological testing of the compound within the invention.

EXAMPLE 1

2-[4-[4-(2,7-Naphthyridin-1-yl)-1-piperazinyl]butyl]-1,2-benzoisothiazol-3(2H)-one 1,1-Dioxide

Step (1) Preparation of 3-Cyano-2,6-dihydroxy-4-methylpyridine

According to the procedure of M. Lounasmoa et al, Tetr. 33, 113 (1977), a solution of cyanoacetimide (80 g, 0.95 mol), ethyl acetoacetate (121 mL, 0.95 mol) and piperidine (94 mL, 0.95 mol) in 320 mL of methanol was heated at reflux for 48 hours. The reaction mixture was concentrated to ½ of it's original volume in vacuo. The precipitate formed was filtered and washed with methanol affording 161 g of a white solid [mp 242° C. (dec)]. The product was generated by dissolving the precipitate in hot $H_2O$, and acidification with concentrated HCl. Upon cooling, the precipitate was filtered, washed with $H_2O$, $CH_3OH$ and dried under high vacuum to give the product (81.6 g, 79%, mp 314°-317° C. with decomposition).

NMR (400 MHz, DMSO $d_6$): δ 2.22 (s, 3H, ArCH₃), 5.58 (s, 1H, ArH).

MS (EI, m/z): 150 (M+, b.p.).

Anal. Calcd. for $C_7H_6N_2O_2$: C, 56.00; H, 4.00; N, 18.70. Found: C, 56.28; H, 4.09; N, 18.52.

Step (2) Preparation of 2,6-Dichloro-3-cyano-4-methylpyridine

According to the procedure of Bobbit et al, J. Org. Chem. 25, 560 (1960) a mixture of 3-cyano-2,6-dihydroxy-4-methylpyridine (20 g, 0.13 mol), and phosphorous oxychloride (48 mL) were sealed in a 500 mL pressure bottle and heated at 180° C. for 5 hours. Upon cooling the bottle was opened and the reaction mixture was poured onto ice. The solids were filtered, washed with $H_2O$ and dried over $P_2O_5$ under vacuum to give the product (23.3 g, mp 108°-109° C., 94%, of suitable purity for use in the next step).

NMR (400 MHz, CDCl₃): δ 2.57 (s, 3H, ArCH₃), 7.27 (s, 1H, ArH).

MS (EI, m/z): 186 (M+, b.p., 2 Cl present), 150 (M-Cl)+.

Step (3) Preparation of 3-Cyano-4-methylpyridine

A mixture of 2,6-dichloro-3-cyano-4-methylpyridine (47 g, 0.25 mol), sodium acetate (41.2 g, 0.5 mol), and palladium (II) chloride (0.5 g) in 220 mL of methanol was hydrogenated on a Parr apparatus under 50 PSI (initial pressure). When the uptake ceased the catalyst was filtered (solka floc) and the filtrate concentrated in vacuo. The crude residue was distilled under vacuum through a Vigreaux column and the product collected at 68°-72° C./2 mm (25.3 g, 85%, as a clear liquid).

NMR (400 MHz, CDCl₃): δ 2.52 (s, 3H, ArCH₃), 7.25 (d, 1H, J=5 Hz, ArH), 8.59 (d, 1H, J=5 Hz, ArH), 8.73 (s, 1H, ArH).

Step (4) Preparation of N,N-Dimethyl-2-(3-cyano-4-pyridyl)etheneamine

A solution of 3-cyano-4-methylpyridine (25 g, 0.21 mol), and N,N-dimethylformamide dimethyl acetal (29.2 mL, 0.22 mol) in dry DMF was heated at reflux overnight. Most of the DMF was removed under reduced pressure. The crude red oil was partitioned between EtOAc (300 mL) and $H_2O$ (300 mL) and the organic phase was washed with $H_2O$, brine and dried ($Na_2SO_4$). Removal of the solvent afforded the product (34.3 g, 94%, as a light red solid of suitable purity for use directly in the next step, mp 80°-83° C.). An analytical sample was prepared by recrystallizing a sample of the crude product from benzene/petroleum ether, (mp 88°-89° C., light red solid).

NMR (400 MHz, CDCl₃): δ 2.98 (s, 6H, NCH₃), 5.23 (d, 1H, J=14 Hz, C=CHN), 7.09 (d, 1H, J=6 Hz, ArH), 7.28 (d, 1H, J=14 Hz, ArCH=C), 8.23 (d, 1H, J=6 Hz, ArH), 8.48 (s, 1H, ArH).

MS (EI, m/z): 173 (M+, b.p.), 158 (M-CH₃)+, 129 [M-N(CH₃)₂], 103, 70.

Anal. Calcd. for $C_{10}H_{11}N_3$: C, 69.43; H, 6.41; N, 24.29. Found: C, 69.18; H, 6.49; N, 23.89.

Step (5) Preparation of 1-Hydroxy-2,7-naphthiridine

A stirred solution of N,N-dimethyl-2-(3-cyano-4-pyridyl)etheneamine (33 g, 0.19 mol) in 200 mL of acetic acid was treated dropwise at 40° C. with 400 mL of 30% hydrobromic acid in acetic acid. After heating at 55°-60° C. for 1.5 hours, the solvents were evaporated under reduced pressure. The residue was diluted with ice cold $H_2O$ and basified with solid $Na_2CO_3$. The aqueous solution was continuously extracted with CHCl₃ overnight. The CHCl₃ layer was dried ($Na_2SO_4$) and the solvent removed in vacuo. The residue was purified by flash chromatography (silica gel 60 Merck, methylene chloride-methanol-ammonia 95:5:1.25) to give the product (17.1 g, 61.5%, mp 262°-265° C., after trituration with isopropanol.

NMR (400 MHz, CDCl₃): δ 6.5 (d, 1H, ArH), 7.3 (t, 1H, ArH), 7.4 (d, 1H, ArH), 8.75 (d, 1H, ArH), 9.6 (s, 1H, ArH), 10.3 (broad, 1H, OH).

Anal. Calcd. for $C_8H_6N_2O$: C, 65.81; H, 4.14; N, 19.19. Found: C, 65.45; H, 4.20; N, 19.20.

This compound has also been described in U.S. Pat. No. 4,176,183.

Step (6) Preparation of 1-Chloro-2,7-naphthyridine

A pressure bottle, equipped with a magnetic stirrer, was charged with 1-hydroxy-2,7-naphthyridine (2.6 g, 17.8 mmol) and 100 mL of phosphorous oxychloride. The bottle was sealed and heated at 130° C. overnight. Upon cooling, the bottle was opened and the excess POCl₃ was removed by evaporation in vacuo. The residue was treated with excess saturated $Na_2CO_3$ and extracted twice with CHCl₃. The organic layer was washed with brine and dried ($Na_2SO_4$). Evaporation of the solvent afforded the product as a light brown solid (2.0 g, 68%, purity 90–95% based on NMR). The product was of suitable purity for use in the next step.

NMR (200 MHz): δ 7.98 (m, 2H, ArH), 8.55 (d, 1H, ArH), 8.87 (d, 1H, ArH), 9.65 (s, 1H, ArH).

MS (EI, m/z): 164 (M)+, 129 (M-Cl)+.

Step (7) Preparation of 1-Piperazinyl-2,7-naphthyridine

A solution of piperazine (5.5 g, 64 mmol) in t-butanol (50 mL) was treated with potassium t-butoxide (0.9 g, 8 mmol) in one portion. After stirring for 10 minutes at 40° C. a solution of 1-chloro-2,7-naphthyridine (1.2 g, 7.3 mmol) in 10 mL of t-butanol was added. Stirring was continued overnight at 40° C. after which the solvent was removed in vacuo. The residue was purified by flash chromatography (silica gel 60 Merck, methylene chloride-methanol-ammonia 9:1:0.125) to give the product (1.0 g, 64%) as a yellow solid.

NMR (200 MHz, CDCl$_3$): δ 3.18 (m, 4H, CCH$_2$N), 3.52 (m, 4H, CCH$_2$N), 7.18 (d, 1H, ArH), 7.58 (d, 1H, ArH), 8.25 (d, 1H, ArH), 8.65 (d, 1H, ArH), 9.5 (s, 1H, ArH).

MS (EI, m/z): 214 (M)+, 146 (b.p.), 129, 85.

Step (8) Preparation of
2-[4-[4-(2,7-Naphthyridin-1-yl)-1-piperazinyl]butyl]-1,2-benzoisothiazol-3(2H)-one 1,1-Dioxide Under an atmosphere of nitrogen, a solution of saccharine (18.3 g, 0.1 mol) in dry DMF (50 mL) was added dropwise to a stirred suspension of sodium hydride (2.4 g, 0.1 mol, washed with petroleum ether) in DMF (100 mL) and stirred at room temperature for 20 minutes. To the solution was added 1,4-dibromobutane (47.5 mL, 0.4 mol) in one portion. The solution was heated at 100° C. for 2 hours and the solvent removed in vacuo. The residue was purified by flash chromatography (silica gel Merck 60, petroleum ether-methylene chloride, gradient elution from 100% petroleum ether to 100% methylene chloride) to give 1-(4-bromobutyl)-1,2-benzoisothiazol-3(2H)-one 1,1-dioxide (30.6 g). The product was recrystallized from isopropanol petroleum ether to give pure product, (15.2 g, 48%) m.p. 45° C.

NMR (400 MHz, CDCl$_3$): δ 1.98 (m, 4H, CCH$_2$CH$_2$C), 3.44 (t, 2H, J=6.3 Hz, CCH$_2$Br), 3.81 (t, 2H, J=6.7 Hz, CCH$_2$N), 7.8–7.93 (m, 3H, ArH), 8.04 (m, 1H, ArH).

MS (EI, m/z): 317 (M)+, 196 (b.p.).

Anal. Calcd. for C$_{11}$H$_{12}$BrNO$_3$S: C, 41.55; H, 3.80; N, 4.40. Found: C, 41.43; H, 3.85; N, 4.48.

This compound is also described in Dompart et al, German Pat. No. 3,321,969.

Under anhydrous conditions, a mixture of 1-piperazinyl-2,7-naphthyridine (0.74 g, 3.46 mmol, prepared by the process of Step 7), 1-(4-bromobutyl)-1,2-benzoisothiazol-3(2H)-one 1,1-dioxide (1.1 g, 3.46 mmol) and potassium carbonate (0.48 g, 3.46 mmol) in 30 mL of chlorobenzene was heated at reflux for 8 hours. The solvent was removed in vacuo and the residue partitioned with CH$_2$Cl$_2$—H$_2$O. The organic phase was washed with brine and dried (Na$_2$SO$_4$). The solvent was evaporated and the residue was purified by flash chromatography (silica gel Merck 60, methylene chloride-methanol-ammonia 97.5:2.5:0.5) to give 0.7 g (45%) of product. Crystallization of two batches of product (1.3 g total) from isopropanol gave 0.95 g, m.p. 152°–153° C., of a light orange solid.

IR (KBr, cm$^{-1}$): 1720, 1740 (C=O).

UV (MeOH, nm): λ$_{max}$285.5 (ε 3600), 325.5 (ε7930), 235.5 (ε 13200).

NMR (400 MHz, CDCl$_3$): δ 1.67 (m, 2H, CCH$_2$C), 1.93 (m, 2H, CCH$_2$C), 2.52 (t, 2H, CCH$_2$N), 2.71 (t, 4H, CCH$_2$N), 3.56 (t, 4H, CCH$_2$N), 3.83 (t, 2H, CCH$_2$N), 7.10 (d, 1H, J=5.3 Hz, ArH), 7.49 (d, 1H, J=5.1 Hz, ArH), 7.8–7.93 (m, 3H, ArH), 8.05 (m, 1H, ArH), 8.24 (d, 1H, J=5.7 Hz, ArH), 8.58 (d, 1H, J=5.7 Hz, ArH), 9.42 (s, 1H, ArH).

MS (EI, m/z): 451 (M)+, 293, 196, 184, 158 (b.p.).

Anal. Calcd. for C$_{23}$H$_{25}$N$_5$O$_3$S: C, 61.18; H, 5.58; N, 15.51. Found: C, 61.02; H, 5.54; N, 15.53.

EXAMPLE 2

The in vitro inhibition of 5-HT$_{1A}$ serotonin receptor binding is used to determine whether the test compound possesses affinity at 5-HT$_{1A}$ receptors and whether there is an indication of gepirone like anxiolytic activity.

The assay is carried out as follows:

Hippocampal tissue from male Sprague Dawley rats is dissected and homogenized on ice in 40 volumes of buffer A (50 mM Tris-HCl, pH=7.7) using a Polytron homogenizer at setting 5 for 3×15-second bursts. The homogenate is then centrifuged at 20,000 rpm (RC5-B; 50,000 g), and the supernatant is discarded. The pellet is resuspended in 40 volumes of the same buffer and incubated at 37° C. for 10 minutes to aid in the removal of endogenous serotonin. The homogenate is then centrifuged (as above) and the supernatant discarded. The pellet is then resuspended in 100 volumes of buffer B (50 mM Tris HCl, pH=7.7 containing 0.1% ascorbate, 10 μM pargyline and 4 mM CaCl$_2$) and sonicated. An aliquot is taken for protein determination by the Lowry method and the remainder stored frozen at −70° C. until used.

The homogenate (50 μL; 0.4–0.6 mg protein/sample) is incubated with 100 μL (1.5–1.8 nM) $^3$H-8-hydroxy-2-(di-n-propylamino)tetraline ($^3$H-8-OH-DPAT) in a final volume of 2 mL of buffer for 10 minutes at 37° C. At the end of the incubation, 3 mL of cold buffer A are added to each tube, and the contents rapidly filtered through Whatman GF/B glass-fiber filters. The filters are then rapidly washed 2 times with 3 mL of the same buffer, placed in scintillation vials, and shaken for 15 minutes with 10 mL of Hydrofluor (National Diagnostics) scintillation cocktail. The vials are then counted in a Packard 460CD scintillation counter.

Specific binding is defined as total binding less binding in the presence of excess unlabeled serotonin (1 μM). Binding in the presence of various concentrations of test drug is expressed as a percent of specific binding when no drug is present. These results are then plotted as logit % binding vs. log concentration of test drug. Linear regression analysis then yields a straight line with 95% confidence limits from which an IC$_{50}$ can be inversely predicted. K$_i$ (inhibition constant) for the test drug is then calculated by the formula:

$$K_i = \frac{IC_{50}}{1 + \frac{[^3H\text{-}8\text{-}OH\text{-}DPAT]}{K_D}}$$

where $K_D$ = 1.8 nM for 8-$OH$-$DPAT$ binding in hippocampus

When tested in this assay, the compounds of this invention gave the results set forth in Table 1.

The results show that the compound of the invention has a high affinity for the 5-HT$_{1A}$ receptor site, evidencing a high potential for anxiolytic activity.

TABLE 1

| Compound | 5-HT$_{1A}$ Receptor Binding % Inhibition at 1 μM or (K$_i$, nM) |
|---|---|
| Example 1 | 100% |
| Gepirone | (65 nM) |
| Buspirone | 94% |

In qualitatively evaluating the above data, high affinity values for 5-HT$_{1A}$ receptors correlate (by analogy with gepirone) with anxiolytic activity, while lower values reflect a lesser activity.

Hence, the compound of this invention is an anxiolytic agent useful in the treatment of anxiety. As such, it may be administered to a patient in need thereof, either neat or with a conventional pharmaceutical carrier.

What is claimed is:

1. A compound having the formula

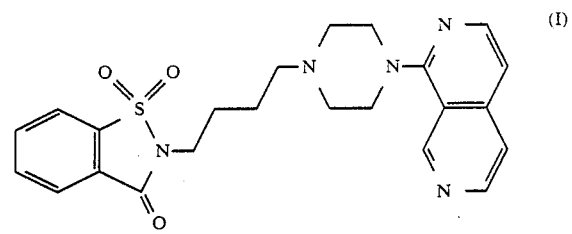

and the pharmaceutically acceptable salts thereof.

2. A method of treating anxiety which comprises administering to a patient suffering from anxiety an effective dosage of a piperazine having the formula (I) as defined in claim 1.

3. A pharmaceutical composition useful for the treatment of anxiety comprising an effective amount of a compound of structure (I), or a pharmaceutically acceptable salt thereof, as defined in claim 1, and a pharmaceutically acceptable carrier.

* * * * *